(12) United States Patent
Marsh

(10) Patent No.: US 10,531,743 B2
(45) Date of Patent: Jan. 14, 2020

(54) ACTIVE CHAIR WITH POSTURE FEEDBACK

(71) Applicant: Robert E Marsh, Kansas City, MO (US)

(72) Inventor: Robert E Marsh, Kansas City, MO (US)

( * ) Notice: Subject to any disclaimer, the term of this patent is extended or adjusted under 35 U.S.C. 154(b) by 0 days.

(21) Appl. No.: 15/971,374

(22) Filed: May 4, 2018

(65) Prior Publication Data

US 2018/0317660 A1     Nov. 8, 2018

Related U.S. Application Data

(60) Provisional application No. 62/502,045, filed on May 5, 2017.

(51) Int. Cl.
| *A47C 9/00* | (2006.01) |
| *A47C 31/12* | (2006.01) |
| *A61B 5/11* | (2006.01) |

(52) U.S. Cl.
CPC .............. *A47C 9/002* (2013.01); *A47C 31/12* (2013.01); *A47C 31/126* (2013.01); *A61B 5/1116* (2013.01)

(58) Field of Classification Search
CPC ........... A47C 9/00; A47C 9/002; A47C 31/12; A47C 31/126; A61B 5/1116
See application file for complete search history.

(56) References Cited

U.S. PATENT DOCUMENTS

| 5,769,492 | A  | * | 6/1998  | Jensen    | A47C 9/002  |
|           |    |   |         |           | 297/188.09  |
| 7,547,067 | B2 | * | 6/2009  | Keilhauer | A47C 3/02   |
|           |    |   |         |           | 297/313     |
| 9,187,013 | B2 | * | 11/2015 | Helm      | B60N 2/002  |
| 9,289,067 | B2 | * | 3/2016  | Meyer     | A47C 7/14   |
| 9,770,107 | B2 | * | 9/2017  | Glockl    | A47C 9/002  |
| 10,213,024| B2 | * | 2/2019  | Reinhard  | A47C 7/14   |
| 2013/0113252 | A1 | * | 5/2013 | Kuenzler | A47C 7/024  |
|           |    |   |         |           | 297/284.3   |
| 2017/0095088 | A1 | * | 4/2017 | Lutwak   | A47C 1/022  |

* cited by examiner

*Primary Examiner* — Philip F Gabler

(57) ABSTRACT

An active chair system incorporates a tilt sensor to detect and measure the tilt of the seat above a pivot point and displays data about that tilt to the user to enable posture corrections to address subtle posture issues that a user might not otherwise recognize.

9 Claims, 2 Drawing Sheets

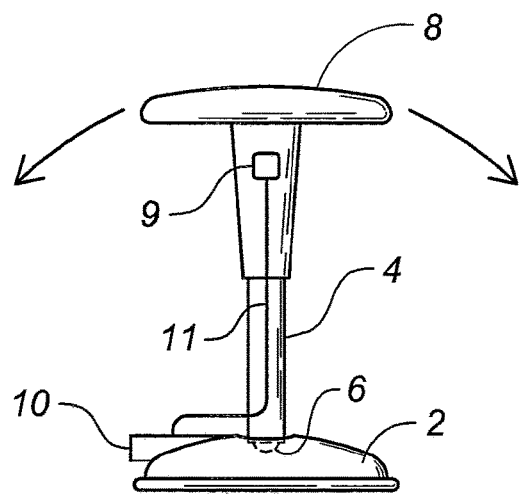
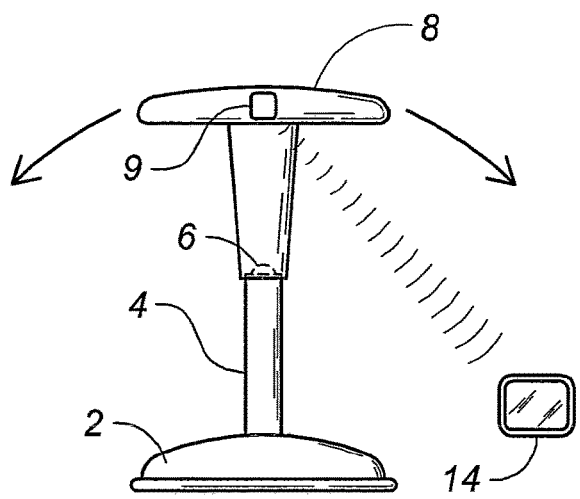
Fig. 1    Fig. 2
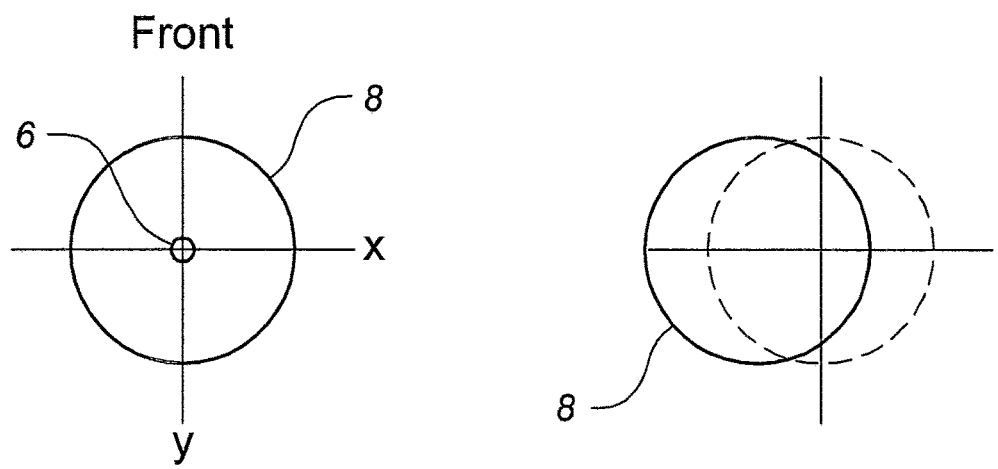
Fig. 3    Fig. 4

ACTIVE CHAIR WITH POSTURE FEEDBACK

BACKGROUND OF THE INVENTION

Increased attention to ergonomics in sedentary office settings has led to the design of chairs that require "active" sitting. These chairs ("active chairs") encourage different kinds of movement, including forward and backward movement, side to side movement, rotation, and wobbling through a 360° range of rotation around a vertical axis. An example of one configuration is shown in U.S. Pat. No. 7,547,067, incorporated by reference. Another example of an active chair is the "ErgoStool" offered by Autonomous Smart Office. The benefits of active sitting and active chairs are well recognized. Most active chairs return to a substantially vertical position when they are not in use.

But there is a significant shortcoming of active chairs that has not been previously recognized—a user may get in the habit of slightly leaning in one direction, with the chair realigned to accommodate this lean by tilting in the opposite direction. The amount of lean and tilt is minor, and would often not be noticed by the user (whose body has subconsciously compensated for the tilt in order to feel balanced). In fact, most users using an active chair would be pleased with the perceived benefits of the chair and would expect that they were sitting straight and improving their posture. An observer would often not notice the lean or resulting body alignment compensation either. But over time this leaning may lead to posture issues, as shown in FIG. 6. In addition, if the active chair is not positioned directly in front of the work surface, a user may not shift the location of the chair and instead try to align themselves with the work surface by leaning to one side or the other, again with negative posture implications.

BRIEF SUMMARY OF THE INVENTION

This invention is an active chair providing posture feedback so that a user can make appropriate posture corrections. Without the recognition of this issue and without the feedback afforded by this invention, there is a real risk of serious and long term posture issues. There is no recognition in the prior art of any importance of monitoring, and providing feedback with respect to, small variations in the vertical orientation of an active chair. While the detection of chair tilt has been recommended (see U.S. Pat. No. 6,392,556) that recommendation is for the very different purpose of providing an alarm when an extreme tilt angle is exceeded to warn of imminent tip over of a conventional four-legged chair. This prior art device—with a chair being intentionally and drastically tipped by a user and a need for warning before falling over—is completely different from the present invention with its objective of detecting and providing feedback to a user of unrecognized detrimental leaning which using an active chair.

This invention is an improvement to an active chair. Active chairs may have several configurations. The most common configuration, as shown in FIG. 1, has a base 2 and a vertical support 4 that is substantially vertical and that may be attached to the base in a manner that permits the vertical support 4 to wobble in some or all directions around a junction 6. A seat 8 is attached to the end of the vertical support 4 that is opposite the base 2. The point around which the support wobbles or tilts is referred to as the "pivot point." The pivot point is at junction 6 adjacent to base 2 in FIG. 1, but may also be in other alternate locations. The pivot point may be above the base as shown in FIG. 2 or approximately adjacent to the seat location as shown in U.S. Pat. No. 8,540,519. Where the chair has an approximately hemispherical base that allows the entire chair to tilt, the pivot point is where the hemispherical base contacts the floor. This invention measures the tilt of the seat above this pivot point and displays data about that tilt to the user to enable posture corrections.

BRIEF DESCRIPTION OF THE SEVERAL VIEWS OF THE DRAWINGS

FIG. 1 is a side view of one embodiment of the invention.
FIG. 2 is a side view of another embodiment the invention.
FIG. 3 is a top view of the invention.
FIG. 4 is a top view of the invention with axes shown.

DETAILED DESCRIPTION OF THE INVENTION

As shown in FIG. 1, the present invention includes a tilt sensor 9 to detect and measure the tilt of the seat. Most broadly, a "tilt sensor" is an instrument for measuring angles of tilt. A "tilt sensor" would include "inclinometers" or any of a variety of well-known devices that detect tilt relative to an axis (sometimes also called inclination or slope). Tilt sensors are well known in the art and various technology options are available, including spirit levels, pendulum based (either solid or liquid) instruments, and micro-electronic-mechanical tilt detectors. The tilt sensor may also be a camera with associated programming to monitor the vertical support position relative to a particular axis or axes. For example, the camera-based tilt sensor could be located in front of or behind the chair and measure tilt around the y axis (side-to-side tilt, when viewed from the front. For convenience, when this description refers to a "tilt sensor" that reference may refer to one tilt sensor, one dual axis tilt sensor, and/or multiple tilt sensors. The data generated by the tilt sensor relating to the tilt of that sensor is referred to as "tilt data."

Figure 6:
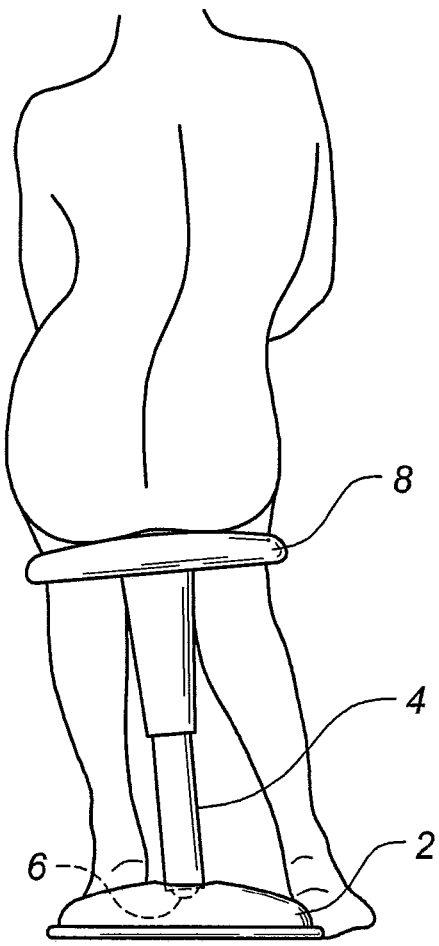
FIG. 6 is side view of the invention showing user posture issues.

As shown in FIG. 3, for purposes of this description, viewing the chair from above, the "x axis" extends to the right and left and the "y axis" to the front and back, with both axes passing through the pivot point—which in the embodiment shown in FIG. 1 is located at junction 6. In use, a person sitting on the chair leaning slightly to the right would cause the seat and post to tilt slightly to the left (see FIG. 6). As the seat tilts around the y axis, the seat is displaced left or right of "center" (with the displacement measured on the x axis). In a fully vertical position, the point represented by the vertical support (viewed from above) would coincide with the intersection of the x and y axes at the pivot point. Preferably the tilt sensor would be digital and preferably would measure tilt around both the x and y axes, although for purposes of addressing posture issues it is tilt around the y axis (left to right displacement) that is most critical. FIG. 4 shows the seat 8 shifted slightly from the vertical position (shown by the dashed outline) as a result of tilt of the vertical support.

A user may also lean forward or backward (tilting around the x axis). Some forward or backward leaning enhances the benefits of active sitting, as does some conscious, balanced side-to-side leaning. But unrecognized and repeated leaning can be harmful. To properly distinguish between side to side, and forward to back tilting (and to align the axes appropriately) it is desirable to calibrate the x and y axes of the seat. This could be accomplished in various manners, including by physical markings on the seat 8 or on the base 2. Alternatively, the axes could be defined and adjusted by the user (by, for example, rotation of a display interface dial to correspond to the sitting position, or by rocking the chair forward and backward to "define" the alignment of the y axis). Alternatively, pressure detectors (well known in the art) located in the seat cushion could detect the sitting bones of the user and define the x axis as the line parallel to the line connecting those sitting bone pressure points. Alternatively, a compass could be incorporated in the seat, base or elsewhere (and preferably adjacent to or contained within the tilt sensor housing) and the direction corresponding to exactly forward facing could be entered in the processor. Some deviations of the measured x and y axes from the ideal alignment shown in FIG. 3 is acceptable. While it might result in minor errors in the magnitude displayed, feedback regarding the existence of tilt and a reasonable degree of tilt data accuracy would be sufficient.

Figure 7:
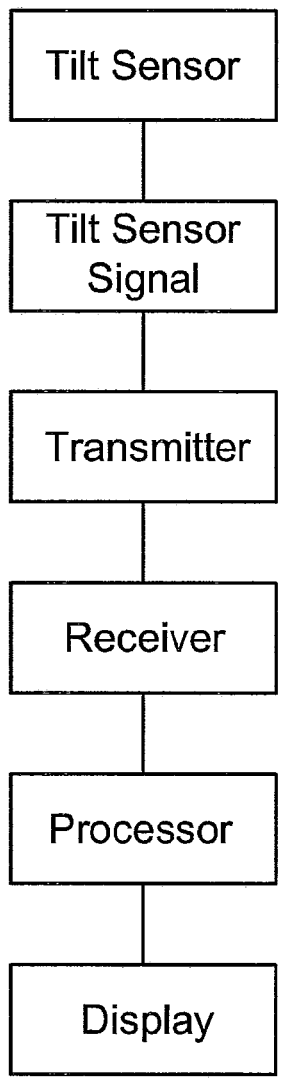
FIG. 7 is a block diagram showing elements of the invention.

The tilt sensor 9 may be attached to the vertical support 4 as shown in FIG. 1 or it may be attached to the seat 8 (or associated seat structure) as shown in FIG. 2. An appropriate power source, such as a battery, may be associated with the tilt sensor in a manner well known in the art, in which case the tilt sensor is an "active tilt sensor." Alternatively, the tilt sensor could be a device that does not require a power supply (called a "passive tilt sensor" in this description). A passive tilt sensor, much like a passive RFID tag, would receive a signal from a reader. The reader would have an antenna and would generate a radiofrequency transmission. The passive tilt sensor would include an antenna as well as an integrated circuit and other components well known in the art. As shown in FIG. 7, the tilt sensor and would utilize RF energy received from the reader to generate and transmit a tilt sensor signal which is received by the reader and is then processed and displayed in a manner well known in the art.

Figure 5:
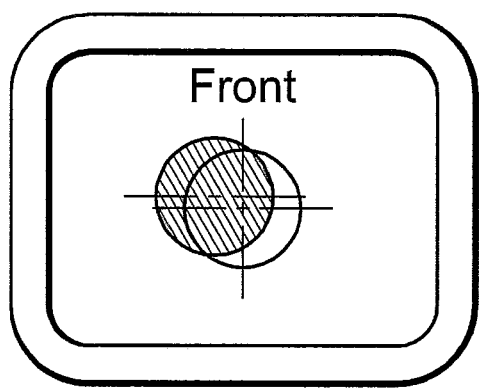
FIG. 5 shows a display screen of the invention.

Another element of the present invention is a user feedback interface. This feedback interface could be a visual feedback provided by a display screen as shown in FIGS. 1, 2 and 5. The display screen presents to the user data from the tilt sensor as transmitted in the tilt sensor signal, either via a wire connection 11 to a display screen 10 attached to the base 2 (as shown in FIG. 1), or to a separate display screen 14 utilizing a radiofrequency (RF) transmitter as shown in FIG. 2. In a preferred embodiment, an RF link, such as a well-known Bluetooth link, is utilized and a smartphone serves as the separate display screen 14. In an embodiment utilizing a passive tilt sensor, the display screen could as associated with the reader receiving the tilt sensor signal as shown in FIG. 7 and could utilize the same power supply. Since the user of the active chair would be sitting in the chair the display would be within a few feet of the tilt sensor and reading of a passive tilt sensor signal would be very feasible. It is also likely that the chair could be in close proximity to a computer and the tilt sensor signal could be received and processed by a connected component of that computer and the display could be provided on the computer monitor.

The display screen 10 or 14 should present tilt around both the x axis and the y axis and displacement would be shown relative to those axes as shown in FIG. 4. The display screen should show the extent of the tilt either numerically (such as in degrees) or graphically, such as with bar charts, an "artificial horizon" type presentation as shown in FIG. 5, or other configurations known in the art. Display screen data should be updated at a high frequency, ideally at least once per second.

In addition to real time visual feedback of current tilt, it may also be desirable to provide "notification" feedback, which could be visual or audible feedback, under certain conditions. Audible feedback could be provided via a speaker associated with the display screen or separately connected to the tilt sensor by wires or a RF connection. Notification events and information could include: (a) when lean in a particular direction has occurred for more than x seconds; or (b) that no significant changes in tilt sensor readings have occurred in the past y seconds (to encourage periodic movement); or (c) the percentage of time that the seat was tilted in a particular direction. These parameters and other desirable parameters could be user defined via a programmable user interface well known in the art. This invention is not intended to sound an alarm if the chair is about to tip over. By their nature active chairs that are the subject of this invention provide clear sensory feedback to the user if they are tilting excessively. It is the subtle, unnoticed tilt, and associated unrecognized posture issues, that are intended to be addressed by this invention.

To conserve power in the case of an active tilt sensor, a motion detector (in any of a variety of configurations known in the art) could be incorporated in the circuitry of this invention to turn on the tilt sensor only when someone is sitting in the chair (which would cause some movement of an active chair). This power conservation would be particularly desirable if the active tilt sensor utilizes an RF transmitter (such as a Bluetooth transmitter) to transmit the tilt sensor signal.

Circuitry and other components for communicating with a remote display are known in the art, such as that described in US Patent Publication No. 2007/0242061 (Rhoten), which is incorporated herein by reference. A radiofrequency link following the Bluetooth protocol, described in detail in US Patent Publication No. 2004/0203379 (Witkowski), would be particularly suitable for one embodiment of the invention. Utilizing a Bluetooth link and suitable mobile smartphone application programmed by any knowledgeable programmer, a user's smartphone could serve as the display screen of the present invention. Circuitry and processing components for generating a tilt sensor signal based on the tilt data are also well known in the art.

I claim:

1. A chair system comprising a seat, a base, a vertical support disposed between said seat and said base, said vertical support having a pivot point enabling tilt and a 360-degree range of rotation around a vertical axis through said pivot point, a tilt sensor for measuring tilt relative to said vertical axis, and a display.

2. The chair system in claim 1 further comprising a processor for generating a tilt sensor signal based on tilt data generated by said tilt sensor and for presenting said tilt data on said display.

3. The chair system in claim 1 with said tilt sensor attached to said vertical support above said pivot point.

4. The chair system in claim 1 with said tilt sensor attached to said seat.

5. The chair system in claim 1 wherein said pivot point comprises a pivot point junction at said base permitting tilt and a 360-degree range of rotation around a vertical axis, with said tilt sensor attached to said vertical support above said pivot point junction.

6. A chair system comprising a seat, a substantially hemispherical base, a vertical support disposed between said seat and said base, said base having a pivot point enabling tilt at the point of contact of said base with a floor surface, and enabling a 360-degree range of rotation around a vertical axis through said pivot point, a tilt sensor for measuring tilt relative to said vertical axis, and a display.

7. The chair system in claim 6 further comprising a processor for generating a tilt sensor signal based on tilt data generated by said tilt sensor and for presenting said tilt data on said display.

8. The chair system in claim 6 with said tilt sensor attached to said vertical support above said pivot point.

9. The chair system in claim 6 with said tilt sensor attached to said seat.

* * * * *